United States Patent [19]

Volles

[11] Patent Number: 4,956,521

[45] Date of Patent: Sep. 11, 1990

[54] ADSORPTION AND ISOMERIZATION OF NORMAL AND MONO-METHYL PARAFFINS

[75] Inventor: Warren K. Volles, Mount Kisco, N.Y.

[73] Assignee: UOP, Des Plaines, Ill.

[21] Appl. No.: 254,156

[22] Filed: Oct. 6, 1988

[51] Int. Cl.[5] .......................... C07C 7/13; C07C 7/135
[52] U.S. Cl. ..................................... 585/826; 585/737; 585/738; 585/739; 585/821; 585/825
[58] Field of Search ............... 585/737, 738, 739, 821, 585/825, 826

[56] References Cited

U.S. PATENT DOCUMENTS

| | | | |
|---|---|---|---|
| 4,073,865 | 2/1978 | Flanigen et al. | 423/325 |
| 4,104,294 | 8/1978 | Grose et al. | 423/326 |
| 4,210,771 | 7/1980 | Holcombe | 585/701 |
| 4,367,364 | 1/1983 | Kulprathipanja et al. | 585/826 |
| 4,423,280 | 12/1983 | Dessau | 585/829 |
| 4,448,671 | 5/1984 | Dessau | 208/26 |
| 4,455,444 | 6/1984 | Kulprathipanja et al. | 585/826 |
| 4,709,116 | 11/1987 | Zarchy et al. | 585/738 |
| 4,717,784 | 1/1988 | Stem et al. | 585/738 |
| 4,855,529 | 8/1989 | Stem et al. | 585/738 |

FOREIGN PATENT DOCUMENTS 0256604 2/1988 European Pat. Off. ............ 585/738

OTHER PUBLICATIONS

Journal of Chromatography, 316 (1984) 333-341.

*Primary Examiner*—Asok Pal
*Attorney, Agent, or Firm*—Thomas K. McBride; John G. Tolomei; Warren K. Volles

[57] ABSTRACT

This invention relates to processes for separating by adsorption lower octane normal and mono-methyl paraffins from hydrocarbon feeds containing normal, mono-methyl and more highly branched paraffin fractions and isomerizing the normal and mono-methyl paraffins to produce higher octane isopentane and more highly branched paraffins. Adsorbents capable of adsorbing both normal and mono-methyl paraffins are used either alone or in combination with adsorbents capable of adsorbing normal paraffins but not mono-methyl paraffins. Isopentane, although adsorbed along with the mono-methyl paraffins, is preferentially eluted from the adsorber and recovered as an adsorption effluent.

26 Claims, 1 Drawing Sheet

ADSORPTION AND ISOMERIZATION OF NORMAL AND MONO-METHYL PARAFFINS

FIELD OF THE INVENTION

This invention relates to processes for separating by adsorption lower octane normal and mono-methyl paraffins from hydrocarbon feeds containing normal, mono-methyl and more highly branched paraffin fractions, and isomerizing the normal and mono-methyl paraffins to produce higher octane isopentane and more highly branched paraffins.

BACKGROUND OF THE INVENTION

Light straight run or virgin naphtha is a hydrocarbon refinery process stream comprising pentane and hexane paraffins and is useful as a blending stock for in gasoline pools. However, the Research Octane Number of this hydrocarbon fraction is relatively low, generally in the range of 68–72. In the past, the octane of this fraction was conveniently raised to about 85–90 RON by the addition of alkyl lead compounds. More recently due to lead phase-down, refiners have implemented other means such as isomerization and reforming to improve the octane of this fraction. Isomerization processes typically produce a product having an octane of about 78–84 RON depending upon the temperature of the reaction. When the isomerization processes are integrated with separation processes such as adsorption or distillation, which separate the effluent from the isomerization reactor into higher and lower octane segments, the final product from the integrated process typically has an octane of about 90 RON. In accordance with the present invention processes are provided for the adsorption and isomerization of a hydrocarbon feed comprising pentane and hexane normal and mono-methyl paraffins which can produce a product having an octane of about 93–96 RON.

Molecular sieve adsorbents have been utilized in a variety of processes in the hydrocarbon processing industry. One area of particular importance is in the field of octane upgrading, where hydrocarbon feedstocks containing pentane and hexane paraffin fractions are separated into high and low octane segments. In general, the normal paraffins and mono-methyl branched paraffins comprise the low octane segment and the more highly branched paraffins (e.g., di-methyl paraffins), naphthenes, and aromatics comprise the high octane segment. However, isopentane, which has a high octane, also has a structure similar to that of the other mono-methyl branched paraffins. Accordingly, the adsorption processes currently existing in the art cannot conveniently separate isopentane and other high octane more highly branched paraffins from the lower octane normal and mono-methyl paraffins, and as a result valuable high octane components may be lost when upgrading the octane of a hydrocarbon feed by adsorption. In addition to the adsorption or separation function, most of the processes used for octane upgrading also incorporate an isomerization process that is used to further isomerize the low octane normal and mono-methyl paraffins to higher octane isopentane and more highly branched paraffins. Some or all of the effluent from the isomerization process can be recycled back to the adsorption process for separation. Alternately, it can be combined with effluent from the adsorption process to form a combined total product.

The adsorption processes known in the art are generally of two types. One type performs a separation of normal from non-normal paraffins using an adsorbent commonly known in the industry as 5A or calcium zeolite A. This process is useful because it can process a hydrocarbon feed containing pentane and hexane paraffin fractions. While there are several variations of this type of process, it has been generally described in U.S. Pat. No. 4,210,771, col. 3, lines 18 to 34 as follows:

"In a broad aspect, the invention provides an integrated TIP process for improving the octane rating of a mixed hydrocarbon feedstock containing saturated paraffins having from 5 to 6 carbon atoms, which comprises passing said feedstock through an isomerization reactor containing a catalyst composition and a hydrogenation component in the presence of hydrogen to convert at least a portion of the normal hydrocarbons in the feedstock to non-normals; the hydrocarbons in the effluent from the reactor are passed to the adsorption section of the system where the normals are adsorbed in a molecular sieve zeolite adsorber bed and the non-normals are eventually passed out of the system as an isomerate product. The adsorber beds, after the adsorption cycle, are desorbed by a hydrogen purge gas producing a desorption vapor effluent containing desorbed normals and hydrogen purge gas."

While this type of process provides substantial benefits, the improvement in octane rating of the product is limited due to the presence in the non-adsorbed fraction of low octane mono-methyl paraffins which are not readily adsorbed by the 5A zeolite.

The other type of adsorption process incorporates an adsorbent that has a slightly larger pore size which allows both normal paraffins and mono-methyl paraffins to be adsorbed but excludes the larger di-methyl branched paraffins. U.S. Pat. No. 4,717,784, e.g., at col. 3, lines 59, et seq., describes an adsorption and isomerization process that upgrades the octane of a $C_6$ (hexane) paraffinic feed by isomerizing the feed and subsequently separating the unreacted normal paraffins and mono-methyl branched paraffins from the di-methyl branched paraffins. This process, however, fails to make any separation of the relatively high octane monomethyl paraffins having not more than five carbon atoms, e.g. isopentane, from the other absorbed hexane and heavier monomethyl paraffins, e.g. 2-methyl pentene, and normal paraffin species. All absorbed mono-methyl paraffins are desorbed along with the normal paraffins and recycled to the isomerizer. The molecular sieve disclosed in U.S. Pat. 4,717,784:

"is a tectosilicate having precise channel dimensions intermediate the channel dimensions present in either the calcium-5A sieve or the ZSM-5 sieve. The molecular sieve of this invention is capable of adsorbing not only normal hexane, but methyl pentanes as well. A preferred molecular sieve of this invention is a tectosilicate having channel dimensions intermediate 5.5×5.5 and 4.5×4.5, but excluding 4.5×4.5 (i.e. calcium 5A) Angstroms."

(See col. 5, lines 42–50).

A most preferred molecular sieve, according to this patent, is ferrierite.

It can be appreciated that in light of the two types of processes described above, processes are sought which can upgrade the octane of a hydrocarbon feedstock containing pentane and hexane paraffinic fractions by separating the low octane normal and mono-methyl paraffins from isopentane and the higher octane, more highly branched paraffins.

In addition to the calcium 5A and ferrierite molecular sieves proposed for use in the octane upgrading processes, other molecular sieves have been proposed to perform separations in other hydrocarbon ranges. For example, in the area of aromatics production zeolites of the type ZSM-5, ZSM-11, ZSM-23, and ZSM-35 have been proposed to separate normal and methyl branched paraffins and olefins from aromatic compounds. See U.S. Pat. No. 4,423,280. U.S. Pat. No. 4,448,671 discloses the use of the same adsorbents to separate waxy linear and methyl branched paraffins from other paraffinic compounds such as, for example, crude oils, heavy oils, distillate oils and lube base oil stocks.

U.S. Pat. Nos. 4,367,364 and 4,455,444 disclose processes whereby normal paraffins are separated from a cyclic and branched chain hydrocarbons by contacting the feed with an adsorbent comprising silicalite. These processes operate at conditions that allow normal paraffins, but not branched chain hydrocarbons, to be adsorbed. U.S. Pat. No. 4,455,444, discloses an example which illustrates that the normal paraffins can be recovered in order of increasing molecular weight, from $n$-$C_{10}$ to $n$-$C_{15}$, by purging with a displacement fluid. The use of the displacement fluid, and subsequent elution of the normal paraffins, is analogous to the use of a carrier fluid in chromatography.

Silicalite has also been proposed for use in column chromatography to isolate mono-methyl alkanes from complex hydrocarbon mixtures. T. C. Hoering and D. H Freeman, *Journal of Chromatography*, 316 (1984) 333-341, disclose adsorbing mono-methyl alkanes on silicalite and then recovering mono-methyl alkanes by desorbing with a normal alkane such as normal octane. The results of the study indicated that silicalite could be used to chromatographically separate methyl alkanes according to their relative adsorptivities in the same way that smaller pore calcium zeolite A could be used to separate normal alkanes according to their relative adsorptivities.

It can readily be appreciated, however, that such chromatographic techniques would not be readily adaptable to commercial scale operation for both technical and economic reasons.

SUMMARY OF THE INVENTION

This invention provides processes for the separation and isomerization of hydrocarbon feeds containing normal paraffins and mono-methyl branched paraffins. One aspect of this invention pertains to processes for separating normal and mono-methyl branched paraffins from a hydrocarbon feed containing normal, mono-methyl, and di-methyl paraffin pentane and hexane fractions which comprises the steps of: passing said hydrocarbon feed through an adsorber bed containing a microporous molecular sieve adsorbent which has an elliptical cross section with pore dimensions between about 5.0 and 5.5 Angstroms along the minor axis and between about 5.5 and 6.0 Angstroms along the major axis, e.g., silicalite, such that normal and mono-methyl branched paraffins including isopentane, are adsorbed and isopentane is preferentially desorbed during continued adsorption to provide a mass transfer zone having isopentane concentrated at the leading edge thereof; removing an essentially non-adsorbed fraction comprising di-methyl branched paraffins from said adsorber bed as an adsorption effluent; eluting at least a portion of the mass transfer zone which comprises isopentane from said adsorber bed as an adsorption effluent; and desorbing said adsorber bed by conventional means including nonadsorbable purge, displacement purge, temperature swing, and pressure swing, to produce a desorption effluent comprising normal and mono-methyl paraffins.

In a further aspect of this embodiment, at least a portion of the hydrocarbon feed is pretreated to remove normal paraffins by passing the hydrocarbon feed through an adsorber bed containing adsorbent having pore dimensions sufficient to allow adsorption of normal paraffins while essentially excluding larger molecules such as mono-methyl paraffins, e.g. calcium zeolite A.

In still a further aspect of this embodiment, at least a portion of the hydrocarbon feed is obtained from an isomerization reactor and at least a portion of the desorption effluent is recycled to the isomerization reactor to form an isomerization reactor effluent comprising normal, mono-methyl branched, and more highly branched paraffins.

Another aspect of this invention pertains to processes for separating isopentane from a hydrocarbon feed containing a pentane fraction which comprises the steps of: passing said hydrocarbon feed through an adsorber bed containing a microporous molecular sieve having eliptical pores with adsorbent cross sectional pore dimensions in the range of approximately 4.5 to 5.5 Angstroms, e.g. ZSM-23, such that isopentane and normal pentane are adsorbed and isopentane is preferentially desorbed during continued adsorption to provide a mass transfer zone having isopentane concentrated at the leading edge thereof; recovering an adsorption effluent and eluting at least a portion of the mass transfer zone which comprises isopentane from said adsorber bed as adsorption effluent; and desorbing adsorbed components as desorption effluent.

DETAILED DESCRIPTION OF THE INVENTION

The fresh feed treated by this process contains normal, mono-methyl, and more highly branched paraffins. It is composed principally of the various isomeric forms of saturated hydrocarbons having from five to about eight, preferably five to six, carbon atoms. Often, the hydrocarbon feed contains at least 40, most frequently 40 to 95 or more, weight percent of such saturated hydrocarbons. The expression "the various isomeric forms" is intended to denote all the branched chain and cyclic forms of the noted compounds, as well as the straight chain forms. Also, the prefix notations "iso" and "i" are intended to be generic designations of all branched chain and cyclic (i.e., non-normal) forms of the indicated compound unless otherwise specified.

The following composition is typical of a feedstock containing 5 to 6 carbon atoms which is suitable for processing according to the invention:

| Components | Mole % |
| --- | --- |
| $C_4$ and lower | 0-7 |
| $i$-$C_5$ | 10-40 |
| $n$-$C_5$ | 5-40 |
| $i$-$C_6$ | 10-40 |
| $n$-$C_6$ | 5-30 |
| $C_7$ and higher | 0-10 |

Suitable feedstocks containing 5 to 6 carbon atoms are typically obtained by refinery distillation operations, and may contain small amounts of $C_7$ and even higher hydrocarbons, but these are typically present, if at all, only in trace amounts. Olefinic hydrocarbons are advantageously less than about 4 mole percent in the feedstock. Aromatic and cycloparaffin molecules have a relatively high octane number. Accordingly, the preferred feedstocks are those high in aromatic and cycloparaffinic hydrocarbons, e.g., at least 3, and more typically from 5 to 25 mole percent of these components combined.

In a preferred aspect, the non-cyclic $C_5$ and $C_6$ hydrocarbons typically comprise at least 60, and more typically at least 75, mole percent of the feedstock, with at least 25, and preferably at least 35, mole percent of the feedstock being hydrocarbons selected from the group of isopentane, iso-hexane and combinations of these. Preferably, the feedstock will comprise no more than 60, and, more preferably, no more than 50 mole percent of a combination of n-pentane and n-hexane.

The processes of the present invention provide for the separation of the low octane normal and monomethyl paraffins from the higher octane more highly branched paraffins and isopentane by adsorption. The molecular sieve used for adsorption in this process must be capable of adsorbing normal paraffins as well as mono-methyl paraffins, for instance, 2-methylpentane and 3-methylpentane, while encluding larger di methyl branded paraffins. Adsorbents that are suitable for this application are those microporous molecular sieves having pores of an elliptical cross section with pore dimensions between about 5.0 and 5.5 Angstroms along the minor axis and between about 5.5 and 6.0 Angstroms along the major axis. A preferred adsorbent for use according to the present invention is silicalite. Silicate, as the term is used herein includes both the silicapolymorph disclosed in U.S. Pat. No. 4,061,724 and also the F-silicalite disclosed in U.S. Pat. No. 4,073,865. Other suitable adsorbents include ZSM-5, ZSM-11, ZSM-48, and other similar crystalline aluminosilicates. ZSM-5 and ZSM-11 are described in U.S. Pat. No. 3,702,886 and Re. No. 29,948 and U.S. Pat. No. 3,709,979, said patents being incorporated herein by reference. In general these adsorbents are high in silica content, the silica to alumina ratio being at least 10 and the preferred adsorbents are more commonly characterized as having silica to alumina ratios higher than 100.

The adsorption section of the present invention contains at least two fixed beds of adsorbent that cyclically undergo stages of adsorption and desorption. During the adsorption step, or steps, feed containing normal pentane; isopentane; 2,3 dimethylbutane (23DMB); 2,2 dimethylbutane (22DMB); 2-methylpentane (2MP); 3-methylpentane (3MP) and normal hexane is introduced into the feed end of a bed containing the adsorbent, e.g., silicalite. (For purposes of discussion and ease of reference, the description is specifically directed to typical $C_5$ to $C_6$ hydrocarbon feed. This is not intended to be in limitation at the broad aspects of the invention.) As the adsorption step progresses, 2,2 dimethylbutane and 2,3 dimethylbutane which are essentially nonadsorbable, pass through the bed and are discharged from the discharge end of the bed. The other feed components are adsorbable to different degrees and form adsorption fronts, or mass transfer zones. The mass transfer zones travel through the bed in an order inverse to their relative adsorptivities. In other words, the less strongly adsorbed components, e.g. isopentane, are preferentially desorbed as more strongly adsorbed components, such as n-pentane, are adsorbed during continued adsorption. Hence, isopentane, being a lesser strongly adsorbed component, is concentrated at the leading edge of the mass transfer zone. An experiment performed with Union Carbide S-115 silicalite adsorbent at a typical adsorption temperature of 260° C. demonstrated the following elution order.

| Components | Breakthrough Time, Min. |
| --- | --- |
| 22DMB | 0.44 |
| 23DMB | 0.88 |
| iC5 | 3.10 |
| nC5 | 4.79 |
| 3MP | 6.14 |
| 2MP | 7.05 |
| nC6 | 12.05 |

The foregoing experiment illustrates that although isopentane is adsorbed by the silicalite, it is less strongly adsorbed than normal pentane, 3-methylpentane, 2-methylpentane and normal hexane and, therefore, elutes faster. Accordingly, the adsorption step, as advantageously practiced according to this invention, can be continued so as to elute at least a portion of the mass transfer zone, which comprises isopentane, from the adsorber bed as an adsorption effluent.

In general, anywhere from about 10 to essentially 100 weight percent of the isopentane contained in the hydrocarbon feed processed according to this invention can be eluted from the adsorber bed as an adsorption effluent. Preferably, however, at least about 50 weight percent, and, most preferably, at least about 80 weight percent of the the isopentane is eluted from the adsorber bed.

Upon completion of the adsorption step, the adsorbent must undergo one or more desorption steps to regenerate the adsorbent. Desorption may be accomplished by any conventional means including nonadsorbable purge, displacement purge, temperature swing, and pressure swing. Conventional means for desorption are well known in the art and are described in the literature. See for example, H. M. Barry, *Chemical Engineering*, 67 No. 3 (1960) 105–107. A preferred method for regenerating the adsorbent is by countercurrent desorption with a nonadsorbable purge gas such as hydrogen. The non-adsorbable purge gas is passed through the adsorber bed and is continued until a major portion of the normal and mono-methyl paraffin components have been desorbed and the bed void space consists principally of nonadsorbable purge gas.

It may be beneficial in some instances to pretreat the adsorber feed to remove the normal paraffins prior to adsorption of the mono-methyl paraffins and isopentane. Adsorbent useful for such pretreatments can be described as having pore dimensions sufficient to allow adsorption of normal paraffins while essentially excluding larger molecules such as mono-methyl paraffins. Particularly suitable zeolites of this type are the A-type zeolites, described in U.S. Pat. No. 2,883,243, which in several of its divalent exchanged forms, notably the calcium cation form, have apparent pore diameters of about 5 Angstroms, and have very large capacities for adsorbing normal paraffins, while excluding monomethyl paraffins. Other suitable molecular sieves include zeolite R, U.S. Pat. No. 3,030,181; zeolite T, U.S. Pat. No. 2,950,952, and the naturally occurring zeolitic molecular sieves chabazite and erionite. These U.S. patents are incorporated by reference herein in their entireties.

In this particular aspect of the invention, the adsorber bed containing, preferably, calcium zeolite A is configured upstream, preferably immediately upstream, of the adsorber bed containing a larger pore sized adsorbent, e.g. silicalite. The two adsorbents can be contained in the same adsorber vessel. It can be appreciated that when the two adsorbents are utilized, the calcium zeolite A adsorber bed can be efficiently desorbed by purging it with the desorption effluent from the larger pore sized adsorbent. Such operation minimizes the amount of non-adsorbable purge gas required since the two adsorber beds are configured in series. Furthermore, such operation is feasible since the desorption effluent from the larger pore adsorbent, which comprises monomethyl paraffins, is not readily adsorbable on the calcium zeolite A.

Another class of adsorbents, those having eliptical pores with cross sectional pore dimensions in the range of approximately 4.5 to 5.5 Angstroms, are useful for separating isopentane from a hydrocarbon feed containing a pentane fraction. Preferred adsorbents for this application are ZSM-23 and ZSM-11 and are described in U.S. Pat. No. 4,076,872 and U.S. Pat. No. 3,709,979. The zeolite ferrierite, as described in U.S. Pat. No. 4,016,425 and U.S. Pat. No. 4,251,499, is also a suitable adsorbent for separating isopentane from a feed containing a pentane fraction. All of the above-mentioned patents are incorporated herein by reference. In this aspect of the invention, the feed, which contains iso and normal pentane, is passed through an adsorber bed containing the above mentioned adsorbent wherein both isopentane and normal pentane are adsorbed and isopentane is preferentially desorbed during continued adsorption to provide a mass transfer zone having isopentane concentrated at the leading edge thereof. The adsorption can be continued so as to recover an adsorption effluent and elute at least a portion of the mass transfer zone, which comprises isopentane, from the adsorber as an adsorption effluent. Regeneration of the adsorbent can be accomplished by desorption by any conventional means including non-adsorbable purge, displacement purge, temperature swing, and pressure swing.

The operating conditions of the adsorbers are generally not critical to performance of the process. However, it will usually be desirable to operate the adsorbers in the temperature range of 40° C. to 400° C., preferably between 100° C. and 260° C., and in the pressure range of 3 bar to 40 bar, preferably between 10 bar and 20 bar.

In addition to the adsorption aspects of the invention, in many instances it will be advantageous to incorporate an isomerization reactor into the process to isomerize the adsorbed normal and mono-methyl paraffins. The isomerization catalyst suitable for use in the process of the present invention includes all catalysts capable of isomerizing normal and mono-methyl branched paraffins to more highly branched chain paraffins. One type can be any of the various molecular sieve-based catalyst compositions well known in the art which exhibit selective and substantial isomerization activity. As a general class, such catalysts comprise the crystalline zeolitic molecular sieves having apparent pore diameters large enough to adsorb neopentane; $SiO_2/Al_2O_3$ molar ratios of greater than 3; and less than 60, preferably less than 20, equivalent percent alkali metal cations wherein those $AlO_4^-$ tetrahedra not associated with alkali metal cations are either not associated with any metal cation, or associated with divalent or other polyvalent metal cations. Exemplary of such zeolites are mordenite and zeolite Y.

Because the feedstock may contain some olefins and will undergo at least some cracking, the zeolitic catalyst is preferably combined with a hydrogenation catalyst component, preferably a metal of group VIII of the Periodic Classification of the Elements (Periodic Table of the Elements, *Handbook of Chemistry and Physics*, 46th edition, The Chemical Rubber Co., 1965–1966). The catalyst composition can be used alone or can be combined with a porous inorganic oxide diluent as a binder material. Suitable catalysts of this type are disclosed in detail in U.S. Pat. Nos. 3,236,761 and 3,236,762. One such catalyst is prepared from a zeolite Y (U.S. Pat. No. 3,130,007) having a $SiO_2/Al_2O_3$ molar ratio of about 5 by reducing the sodium cation content to less than about 15 equivalent percent by ammonium cation exchange, then introducing between about 35 and 50 equivalent percent of rare earth metal cations by ion exchange and thereafter calcining the zeolite to effect substantial deammination. As a hydrogenation component, platinum or palladium in an amount of about 0.1 to 1.0 weight percent, can be placed on the zeolite by any conventional method. The disclosures of these above-cited U.S. patents are incorporated herein by reference in their entireties. A preferred zeolite isomerization catalyst for use according to this invention is I-7 isomerization catalyst available from UOP, Des Plaines, Ill.

Another suitable type of isomerization catalyst which may be used in this process is a composite of a metal from group VIII of the Periodic Table with a solid support. The platinum group metals, and platinum in particular, are preferred for use as components of such a catalyst in this process. Solid supports which are suitable for a catalyst of this type include silica, alumina, magnesia, zirconia, chromia, etc. A preferred support or carrier material is alumina. It is also preferred that this type of catalyst incorporate a halogen component into the catalyst composite to impart additional acidity and activity to the catalyst. This combined halogen may be either fluorine, chlorine, iodine, bromine, or mixtures thereof. Chlorine is the most preferred halogen for purposes of the present invention and will be typically combined with the carrier material sufficient to result in a final composite that contains preferably about 0.1 to 5.0 total weight percent halogen. In addition, small amounts of halogen, such as in the form of carbon tetrachloride, may be continuously added to the catalyst to offset any halogen loss. In some instances, it may be beneficial to impregnate the catalyst with an anhydrous Friedel-Crafts type metal halide, such as aluminum chloride. Catalysts of this type are disclosed in detail in U.S. Pat. Nos. 2,999,074, and 3,772,397 and are incorporated herein by reference. A preferred isomerization catalyst of the halogenated type is I-8 isomerization catalyst available from UOP, Des Plaines, Ill.

In general, the isomerization reaction can be carried out in the vapor phase when either of the two catalyst types is used, although complete vaporization does not need to be maintained when the halogenated catalyst is used. The operating temperature of the isomerization reactor is generally within the range of 40° C. to 400° C. and, more specifically, in the range of 100° C. to 200° C. for the halogenated catalyst and 200° C. to 400° C. for the noble metal zeolite catalyst. The operating pressure is typically within the range of 3 bar to 40 bar but is not critical to the isomerization performance. However, it is generally desirable to operate the isomerization reactor in the range of 10 bar to 20 bar in order to be compatible with the adsorption section which preferentially operates in the range of 10 bar to 20 bar. The hydrocarbon flowrate through the isomerization reactor is generally maintained at a weight hourly space velocity from 0.5 to 5.0 hr$^{-1}$, and, more typically, from 0.5 to 3.0 hr$^{-1}$. In order to prevent catalyst coking a hydrogen partial pressure in the range of 3 to 20 bar, and, more preferably, in the range 6 to 14 bar should be maintained over the isomerization catalyst.

When the adsorption process of the present invention is practiced in conjunction with the isomerization process of the present invention, several configurations are possible. One configuration is known as a reactor lead process and is described in U.S. Pat. No. 4,210,771. In the reactor lead process, the feed is passed through the isomerization reactor prior to being passed through the adsorbers. Desorption effluent from the adsorbers is then combined with feed and passed through the isomerization reactor. Another configuration is known as the adsorber lead process and is described in U.S. Pat. No. 4,709,116. In the adsorber lead process, the feed is passed through the adsorbers prior to being passed through the isomerization reactor. At least a portion of the effluent from the isomerization reactor is then combined with feed and passed through the adsorbers. A third configuration involves a split feed process wherein a portion of the feed is initially passed through the isomerization reactor, and another portion is initially passed through the adsorbers.

It will also be understood that certain combinations of adsorbent type and catalyst are preferred. For example, it is generally known that zeolite calcium A adsorbent is sensitive to acid attack. In U.S. Pat. No. 3,150,205, at col 2, lines 36 to 46, it was disclosed that:

"It is necessary that the isomerate be substantially free of hydrogen halides when charged to the adsorbent material in that the adsorbent materials useful herein are generally adversely affected and even attacked by hydrogen halides. Thus, where the isomerization process is promoted with hydrogen halide, means should be provided, as a portion of the isomerization process, for removal of hydrogen halides: a bed of alumina or other material which will react with hydrogen halides may be advantageously provided in the effluent stream from the isomerization reaction."

Accordingly, the use of halogen activated isomerization catalysts is frequently avoided when calcium A zeolite adsorbent is used unless there are appropriate means for removal of the halides as described above. A preferred combination according to the present invention is to use one of the larger pore, high silica adsorbents described supra, e.g., silicalite or ZSM-5, with a halide activated isomerization catalyst. Because of their high silica-low alumina content, adsorbents of this type possess a unique acid-resistant characteristic and removal of the halides is not required. Another preferred combination is to use one of the larger pore, high silica adsorbents such as silicalite or ZSM-5 in conjunction with a smaller pore calcium A zeolite adsorbent as hereinbefore described with an isomerization catalyst that is not halide activated.

EXAMPLE

Figure 1:
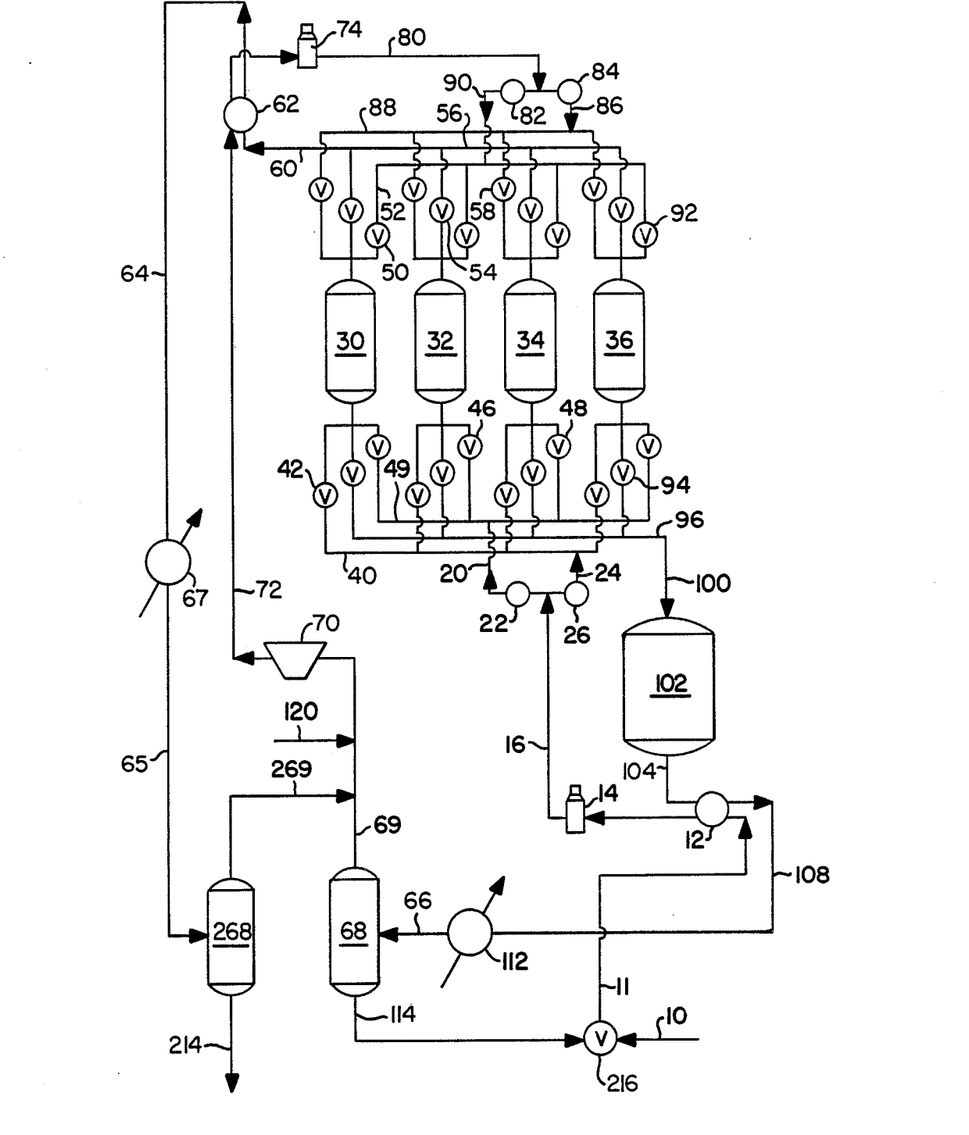
FIG. 1 is a schematic of a process according to the invention wherein an integrated adsorption-isomerization process is used to upgrade the octane of a hydrocarbon feed comprising a pentane and hexane paraffin fraction.

For purposes of illustrating the invention, the following description and example of an integrated adsorption-isomerization process is provided in conjunction with the drawing. The example should not be considered a limitation to the processes of the present invention. The fresh feed to the process has a Research Octane Number of 64 and the following composition:

| Component | Mole Percent |
|---|---|
| iC$_4$ | 0.2 |
| nC$_4$ | 4.0 |
| iC$_5$ | 18.4 |
| nC$_5$ | 28.9 |
| CP (cyclopentane) | 1.2 |
| 22DMB | 0.4 |
| 23DMB | 1.0 |
| 2MP | 7.4 |
| 3MP | 4.5 |
| nC$_6$ | 26.3 |
| MCP (methylcyclopentane) | 4.1 |
| CH (cyclohexane) | 3.0 |
| BZ (benzene) | 0.4 |
| C$_7$+ | 0.2 |

The fresh hydrocarbon feed is fed via Line 10 at a rate of 280.7 kgmol/hr to Valve 216 where it mixes with the reactor effluent condensate from Line 114, to form the adsorber feed at a rate of 799.1 kgmol/hr. The adsorber feed in Line 11 is heated by indirect heat exchange with reactor effluent in Heat Exchanger 12 from which it is passed to Furnace 14 where it is heated to approximately 260° C. for passage to the adsorption section via Line 16.

Adsorber feed from Line 16 and Furnace 14 are directed partially to Line 20 by way of Pressure Control Valve 22 and partially to Line 24 by means of Flow Rate Control Valve 26. From these lines the adsorber feed stream is directed to the appropriate bed in the adsorption section. Each of the four adsorber beds contains 30849 kg of Union Carbide calcium zeolite A adsorbent in the form of 1/16 inch cylindrical pellets in the feed end of the adsorber bed and 24092 kg of Union Carbide S-115 silicalite adsorbent in the form of 1/16 inch cylindrical pellets in the remaining portion of the adsorber bed. In a four-bed system, each of the beds cyclically undergoes the stages of:

A-1 adsorption fill, wherein the vapor in the bed void space consists principally of a nonadsorbable purge gas, preferably hydrogen, is forced from the bed void space by the incoming hydrocarbon feed without substantial intermixing thereof with nonadsorbed feed fraction;

A-2 adsorption, wherein the feed is cocurrently passed through said bed and the normal and monomethyl paraffins including isopentane in the feed are selectively adsorbed while the nonadsorbed components of the feedstock are removed from the bed as adsorption effluent and during such adsorption isopentane is preferentially desorbed during continued adsorption to provide a mass transfer zone having isopentane concentrated at the leading edge thereof, and eluting at least a portion of the mass transfer zone, which comprises isopentane, from the adsorber bed as adsorption effluent;

D-1 purging, wherein the adsorbent which is loaded with essentially normals in the calcium zeolite A section and essentially hexane mono-methyl paraffins in the silicalite section and containing in the bed void space essentially a feedstock mixture, is purged countercurrently, with respect to the direction of A-2 adsorption by passing through the bed a nonadsorbable purge gas, preferably hydrogen, in the form of a hydrogen-containing recycle stream which comprises hydrogen and light hydrocarbons, in sufficient quantity to remove said void space feedstock vapors in the bed effluent;

D-2 purge desorption, wherein the selectively adsorbed feedstock normals and mono-methyl paraffins are desorbed as part of the desorption effluent by passing a nonadsorbable purge gas, preferably hydrogen in the form of a hydrogen-containing recycle stream which comprises hydrogen and light hydrocarbons, through the bed countercurrently with respect to the A-2 adsorption step until the major portion of the adsorbed components have been desorbed and the bed void space vapors consist principally of the nonadsorbable purge gas.

Referring again to the drawing, and the adsorption section in particular, the following description details an operation wherein Bed 30 is undergoing A-1 adsorption-fill; Bed 32, A-2 adsorption; Bed 34, D-1 void space purging and Bed 36, D-2 purge desorption. A portion of the adsorber feed from Line 16 is directed via Line 24 through Manifold 40 and Valve 42 to Adsorption Bed 30 undergoing A-1 adsorption.

Bed 30, at the time that feed passing through Valve 42 enters, contains residual purge gas from the preceding desorption stage. The purge gas is typically hydrogen-containing because of the desire to maintain at least a minimum hydrogen partial pressure in the isomerization reactor. This purge gas is supplied to the adsorbers during desorption as a purge gas recycle stream via Line 80. The rate of flow of the adsorber feed through Line 24, Manifold 40 and Valve 42 is controlled such that Bed 44 is often flushed of residual hydrogen-containing purge gas adsorber stage time period of, for instance, from about thirty seconds to about two minutes.

During this first stage of adsorption in Bed 30, the hydrogen-containing purge gas effluent passes from the bed through Valve 50 into Manifold 52. During the time period when the hydrogen-containing purge gas is being flushed from Bed 30, the remaining adsorber feed passes through Valve 22 and Line 20, through Manifold 44 and Valve 46 to Bed 32.

The normal and mono-methyl paraffins are adsorbed by Bed 32 which is undergoing A-2 adsorption and an adsorber effluent, i.e., the nonadsorbed non-normals and adsorbed isopentane emerges from the bed through Valve 54 and from there is fed to Manifold 56. The adsorber effluent flows through Line 60, Heat Exchanger 62 and Line 64 at a rate of 389.7 kgmol/hr and is then further cooled to 38° C. in Heat Exchanger 67 and flows through Line 65 to Separator 268 where the liquid product is withdrawn at a rate of 309.0 kgmol/hr and the overhead vapors flow through Line 269 to be recycled as purge gas.

The purge gas from Line 269 at a rate of 80.7 kgmol/hr is combined with the purge gas from Line 69 and make-up purge gas from Line 120 at a rate of 30.2 kgmol/hr and passed through Compressor 70 at a combined rate of 1498.2 kgmol/hr.

From Compressor 70, the hydrogen containing purge gas is passed through Line 72 and Heat Exchanger 62 and Heater 74, wherein it is heated to a temperature of approximately 260° C. and then passed through Line 80 as the purge gas recycle stream. The pressure of the adsorbers will typically be within the range of from 13.6 to 21.8 bar, and preferably will be in the range of from 16.3 to 20.4 bar.

The hydrogen-containing purge gas recycle stream from Line 80 can be divided into two streams by means of Flow Control Valves 82 and 84, and the lesser stream passed through Line 86, Manifold 88 and Valve 58 countercurrently (with respect to the previous adsorption stroke) through Bed 34. The low, controlled flow rate employed for the first stage desorption is for the purpose of flushing nonadsorbed hydrocarbons from the bed voids without causing excessive desorption of the normals from the adsorbent.

The effluent from Bed 34 passes through Valve 48 and into Manifold 44 where it is recycled through Valve 46 directly to Bed 32 undergoing A-2 adsorption. The major portion of the hydrogen recycle stream from Line 80 is passed through Control Valve 82, Line 90, to Manifold 52 where it is mixed with the previously mentioned first stage adsorption effluent from Valve 50 and then passes through Valve 92 and Bed 36. During this stage, selectively adsorbed normal and mono-methyl paraffins are desorbed from the molecular sieve and flushed from the bed. The desorption effluent from Bed 36, comprising hydrogen and desorbed paraffins, passes through Valve 94 and Manifold 96 to Line 100, from which it is sent to the Isomerization Reactor 102 as reactor feed.

The foregoing description is for a single adsorber stage time period of a total four-stage cycle for the system. For the next adsorber stage time period, appropriate valves are operated so that Bed 30 begins A-2 adsorption, Bed 32 begins D-1 purging, Bed 34 begins D-2 desorption and Bed 36 begins A-1 adsorption. Similarly, a new cycle begins after each adsorber stage time period; at the end of the four cycle time periods, all the beds have gone through all stages of adsorption and desorption.

The following chart illustrates the functioning of each of the four beds for adsorption stage cycle times of one minute.

| Time, Min. | 0-1 | 1-2 | 2-3 | 3-4 |
| --- | --- | --- | --- | --- |
| Bed 30 | A-1 | A-2 | D-1 | D-2 |
| Bed 32 | A-2 | D-1 | D-2 | A-1 |
| Bed 34 | D-1 | D-2 | A-1 | A-2 |
| Bed 36 | D-2 | A-1 | A-2 | D-1 |

The isomerization process will result in some hydrogen losses from the purge gas due to hydrogenation of starting materials and cracked residues. Hydrogen will also be lost due to solubility in product, and possibly a vent from Line 69 (not shown) which can be controlled by suitable valve means. These losses require the addition of make-up hydrogen. Make-up hydrogen can be supplied in impure form, typically as an off gas from catalytic reforming or steam reforming of methane.

These hydrogen sources are suitably pure for isomerization processes which typically have a vent from the recycle stream. Refinery streams of lesser purity may also be satisfactory. The desorption effluent in Line 100 will comprise desorbed normal and monomethyl paraffins, e.g., n pentane, n-hexane, 2-methylpentane, 3-methylpentane and hydrogen and light hydrocarbons and other impurities which comprise the purge gas used for desorption. This effluent is reactor feed and is passed to Isomerization Reactor 102.

Isomerization Reactor 102 contains a mordenite base isomerization catalyst available from UOP, Des Plaines, Ill. The effluent from Reactor 102 flows through Heat Exchanger 12 and Water Cooler 112 at a rate of 1905.7 kgmol/hr to Separator 68 where liquid is withdrawn through Line 114 and combined with fresh feed at Valve 216.

The liquid product withdrawn from Separator 268 after stabilization has a Research Octane Number of 93.5 RON and the following composition:

| Component | Mole Percent |
| --- | --- |
| $iC_4$ | 2.6 |
| $nC_4$ | 1.5 |
| $iC_5$ | 52.4 |
| $nC_5$ | 0.5 |
| CP | 1.4 |
| 22DMB | 19.7 |
| 23DMB | 11.0 |
| 2MP | 0.7 |
| 3MP | 1.5 |
| $nC_6$ | 0.5 |
| MCP | 4.4 |
| CH | 3.1 |
| BZ | 0.4 |
| $C_7+$ | 0.3 |

Those skilled in the prior art will readily appreciate that the basic invention can be practiced within the scope of the appended claims in ways other than as described in detail above. For example, the adsorbers can be operated so as to allow a portion of the normal paraffins or mono-methyl branched paraffins to elute from the adsorber along with isopentane. Operation in such a mode would result in a lower product octane, but also would reduce the adsorbent inventory and associated operating and equipment costs.

What is claimed is:

1. A process for separating isopentane and di-methyl branched hexane paraffins from a hydrocarbon feed containing isopentane, mono-methyl branched hexane paraffins, and di-methyl branched hexane paraffins, which comprises the steps of:
   (a) passing said hydrocarbon feed through an adsorber bed containing a microporous molecular sieve adsorbent having pores of an elliptical cross-section with pore dimensions between about 5.0 and 5.5 along the minor axis and between about 5.5 and 6.0 along the major axis, wherein mono-methyl branched hexane paraffins and isopentane are adsorbed and isopentane is preferentially desorbed during continued adsorption to provide a mass transfer zone having isopentane concentrated at the leading edge thereof;
   (b) removing an essentially non-adsorbed fraction comprising di-methyl branched hexane paraffins from said adsorber bed as a portion of an adsorption effluent;
   (c) eluting at least a portion of the mass transfer zone which comprises isopentane from said adsorber bed as another portion of the adsorption effluent; and
   (d) desorbing mono-methyl branched hexane paraffins from said adsorber bed to regenerate the adsorber bed and produce a desorption effluent comprising mono-methyl branched hexane paraffins.

2. A process according to claim 1 wherein said adsorbent comprises silicalite.

3. A process according to claim 1 wherein said adsorbent comprises ZSM-5.

4. A process according to claim 1 wherein the feed further comprises normal pentane and normal hexane.

5. A process according the claim 4 wherein said hydrocarbon feed is pretreated to remove normal pentane and hexane paraffins by passing said hydrocarbon feed through an adsorber bed containing adsorbent having pore dimensions sufficient to allow adsorption of normal paraffins while essentially excluding mono-methyl branched paraffins.

6. A process according to claim 5 wherein said adsorbent is calcium zeolite A.

7. A process according to claim 5 wherein said adsorber bed of claim 5 is configured immediately upstream of the said adsorber bed of claim 1.

8. A process according to claim 7 wherein the adsorber beds are desorbed by passing a non-adsorbable purge gas through said adsorber beds in a reverse order to the passing of said hydrocarbon feed.

9. A process to claim 1 wherein at least a portion of the hydrocarbon feed is obtained from an isomerization reactor and at least a portion of the desorption effluent is recycled to the isomerization reactor to form an isomerization reactor effluent comprising normal, mono-methyl branched, and di-methyl branched paraffins.

10. A process according to claim 9 wherein the isomerization reactor contains an isomerization catalyst which comprises a crystalline zeolite molecular sieve and a Group VIII metal.

11. A process according to claim 10 wherein the crystalline zeolite molecular sieve is mordenite and the Group VIII metal is platinum.

12. A process according to claim 9 wherein the isomerization reactor contains an isomerization catalyst which comprises a porous carrier material or support in combination with a Group VIII metal and a halogen component.

13. A process according to claim 12 wherein the porous carrier material or support is alumina, the Group VIII metal is platinum, and the halogen component is chlorine.

14. A process for separating isopentane from a hydrocarbon feed containing a pentane fraction which comprises the steps of:
   (a) passing said hydrocarbon feed through an adsorber bed containing a microporous molecular sieve having elliptical pores with cross-sectional pore dimensions in the range of approximately 4.5 to 5.5, wherein isopentane and normal pentane are adsorbed and isopentane is preferentially desorbed during continued adsorption to provide a mass transfer zone having isopentane concentrated at the leading edge thereof;
   (b) eluting at least a portion of the mass transfer zone, which comprises isopentane from said adsorber bed as an adsorption effluent; and
   (c) desorbing adsorbed components from said adsorber bed to regenerate the adsorber bed and produce a desorption effluent comprising said components.

15. A process according to claim 14 wherein said adsorbent comprises ZSM-23.

16. A process according to claim 14 wherein said adsorbent comprises ZSM-11.

17. A process according to claim 14 wherein said adsorbent comprises ferrierite.

18. A process according to claim 1 wherein the separation is performed in an adsorption section comprising at least two adsorber beds which undergo a cyclical sequence of adsorption and desorption steps.

19. A process according to claim 4 wherein normal pentane and normal hexane are adsorbed in said adsorber bed and desorbed from said adsorber bed along with the mono-methyl branched hexane paraffins.

20. A process for separating isopentane and di-methyl branched hexane paraffins from a hydrocarbon feed comprising isopentane, normal pentane, normal hexane, mono-methyl branched hexane paraffins and di-methyl branched hexane paraffins which comprises the steps of:
(a) passing said hydrocarbon feed to a first adsorber bed containing adsorbent having pore dimensions sufficient to allow adsorption of normal paraffins while essentially excluding mono-methyl and di-methyl branched paraffins, wherein normal pentane and normal hexane are adsorbed to provide a de-normalized feed at least partially depleted in normal paraffins and comprising isopentane, mono-methyl branched hexane paraffins and di-methyl branched hexane paraffins;
(b) passing said de-normalized feed through a second adsorber bed containing adsorbent having pore dimensions sufficient to allow adsorption of isopentane and mono-methyl branched hexane paraffins while essentially excluding di-methyl branched hexane paraffins, wherein isopentane and mono-methyl branched hexane paraffins are adsorbed and isopentane is preferentially desorbed during continued adsorption to provide a mass transfer zone having isopentane concentrated at the leading edge thereof;
(c) removing an essentially non-adsorbed fraction comprising di-methyl branched hexane paraffins from said second adsorber bed as a portion of an adsorption effluent;
(d) eluting at least a portion of the mass transfer zone which comprises isopentane from said adsorber bed as another portion of the adsorption effluent; and
(e) desorbing mono-methyl branched hexane paraffins from said second adsorber bed and normal pentane and hexane from said first adsorber bed.

21. A process according to claim 20 wherein the adsorbent in the second adsorber bed comprises a microporous molecular sieve adsorbent having pores of an elliptical cross-section with pore dimensions between about 5.0 and 5.5 along the minor axis and between about 5.5 and 6.0 along the major axis.

22. A process according to claim 21 wherein the adsorbent in the second adsorber comprises silicalite, ZSM-5 or mixtures thereof.

23. A process according to claim 20 wherein the adsorbent in the second adsorber bed comprises a microporous molecular sieve having elliptical pores with cross-sectional pore dimensions in the range of approximately 4.5 to 5.5.

24. A process according to claim 23 wherein the adsorbent in the second adsorption zone comprises ferrierite, ZSM-23, ZSM-11 or mixtures thereof.

25. A process according to claim 20 wherein the adsorbent in the first adsorption zone comprises Zeolite 5A.

26. A process according to claim 1 comprising admixing at least a portion of the adsorption effluent with other gasoline blending stock components to produce a gasoline.

* * * * *

UNITED STATES PATENT AND TRADEMARK OFFICE
CERTIFICATE OF CORRECTION

PATENT NO. : 4,956,521
DATED : September 11, 1990
INVENTOR(S) : Warren K. Volles It is certified that error appears in the above-identified patent and that said Letters Patent is hereby corrected as shown below:

In Claim 1, col. 13, line 56, after "5.5", first occurrence, insert -- Angstroms --.

In Claim 1, col. 13, line 57, after "6.0" insert -- Angstroms --.

In Claim 14, col. 14, line 59, after "5.5" insert -- Angstroms --.

In Claim 21, col. 16, line 19, after "5.5" insert -- Angstroms --.

In Claim 21, col. 16, line 20, after "6.0" insert -- Angstroms --.

In Claim 23, col. 16, line 28, after "5.5" insert -- Angstroms --.

Signed and Sealed this

Eighteenth Day of February, 1992

Attest:

HARRY F. MANBECK, JR.

*Attesting Officer*     *Commissioner of Patents and Trademarks*